United States Patent [19]

Rector

[11] 4,240,186
[45] Dec. 23, 1980

[54] FRENUM LOCK

[76] Inventor: Charles W. Rector, 3304 Russel Rd., Centralia, Wash. 98531

[21] Appl. No.: 77,679

[22] Filed: Sep. 21, 1979

[51] Int. Cl.³ .......................................... A01N 1/00
[52] U.S. Cl. .................................................. 27/21
[58] Field of Search ........................................ 27/21

[56] References Cited

U.S. PATENT DOCUMENTS

| | | | |
|---|---|---|---|
| 2,120,143 | 6/1938 | Divel | 27/21 |
| 2,587,292 | 2/1952 | De Voe | 27/21 |
| 3,103,052 | 9/1963 | Rector | 27/21 |
| 3,195,215 | 7/1965 | Rector | 27/21 |
| 3,205,553 | 9/1965 | Pfeifer | 27/21 |

Primary Examiner—John D. Yasko
Attorney, Agent, or Firm—Thomas W. Secrest

[57] ABSTRACT

This invention is directed to a frenum lock, also known as a natural expression former, for use by morticians. It relates to an improvement on two of my patents. I have a patent entitled "NATURAL EXPRESSION FORMER", U.S. Pat. No. 3,103,052, issuing date of Sept. 10, 1963 and a patent entitled "NATURAL EXPRESSION FORMER WITH BITE INDENTATION", U.S. Pat. No. 3,195,215, issuing date of July 20, 1965. The improvement of this invention is the positioning of the dividing lines in the central portion of the natural expression former or the frenum lock. The dividing lines in the central portion of the frenum lock permit wider spreading of the expression forming wing-like portions on insertion of the expression former into the mouth of the corpse or cadaver and permit greater adaptation of the expression former to the dental arch of the corpse or the cadaver.

12 Claims, 6 Drawing Figures

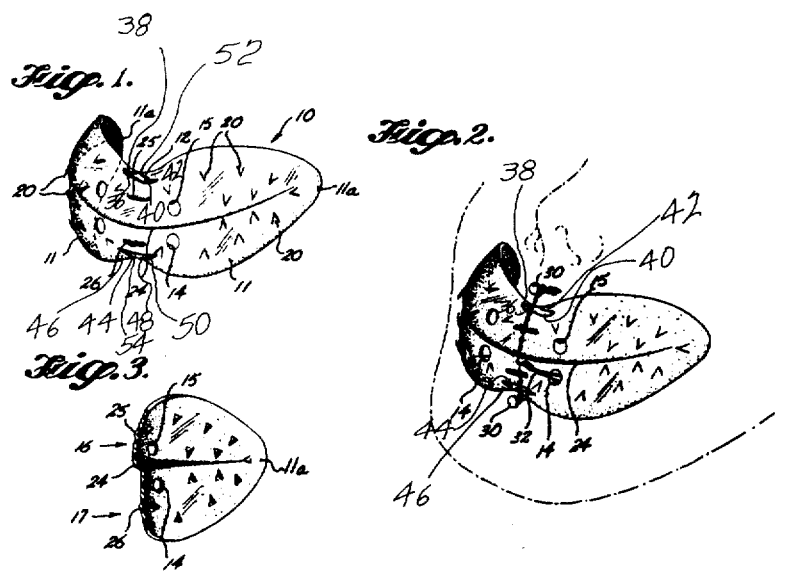
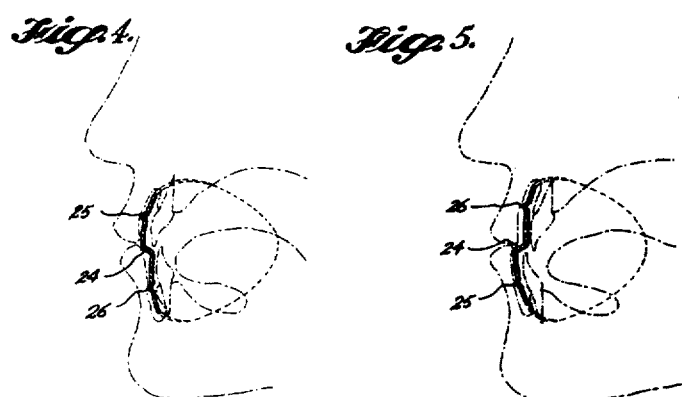
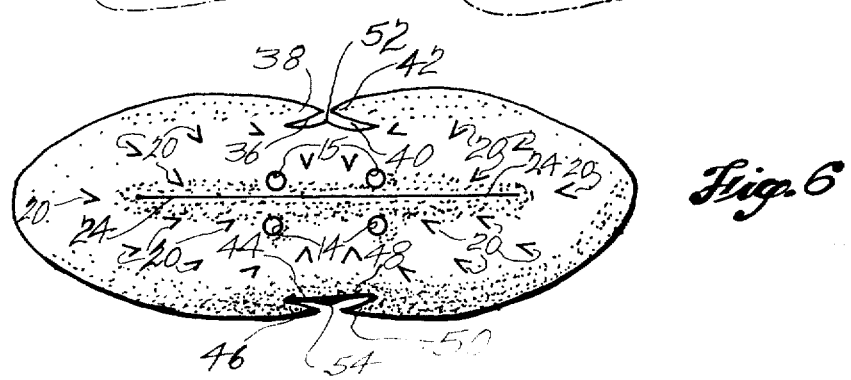

FRENUM LOCK

A BRIEF DESCRIPTION OF THE INVENTION

My two U.S. Pat. No. 3,103,052, and No. 3,195,215 disclose a natural expression former. This invention is an improvement on the inventions of these two enumerated patents.

This invention makes it easier to use and to insert and to position the expression former into the mouth of the corpse or the cadaver. The central portion of the expression former is formed so as to have dividing lines moving away from the outer edge of the central portion so as to form flaps. These dividing lines permit wider spreading of the expression forming wing-like portions of the former upon insertion of the former into the mouth of the corpse or the cadaver and also permit greater adaptation of the former to the dental arch of the corpse or cadaver.

These dividing lines and flaps make it easier to work the expression former into the mouth of the cadaver and also make it possible for the cadaver to have a more natural appearance around the mouth and the lips.

IN THE DRAWINGS

In the drawings it is seen that:

FIG. 1 is a perspective view of a natural expression former or frenum lock embodying the improvement of this invention, viz., dividing lines and flaps, in the central portion of the frenum lock;

FIG. 2 is a perspective view of the improved expression former shown in relation to the features of a corpse and showing its relationship to injector needles and wires normally used with the expression former or frenum lock;

FIG. 3 is a transverse sectional view taken through the mid-line of the frenum lock, which for clarity of illustration, is shown with somewhat exaggerated thickness;

FIG. 4 is a sectional view of the frontal portion, only, of the expression former, with the outline of the entire former shown by dotted lines, as inserted in the mouth of a corpse having a natural overbite;

FIG. 5 is a sectional view of the frontal portion, only, of the expression former, with the outline of the entire former shown by dotted lines, as inserted in the mouth of a corpse having a natural underbite; and, FIG. 6 is a front elevational view of the frenum lock or expression former, drawn to, approximate, exact scale.

THE SPECIFIC DESCRIPTION OF THE INVENTION

The frenum lock or natural expression former of this invention comprises many of the characteristics of the expression former of my two U.S. Pat. Nos. 3,103,052 and 3,195,215. Reference will be made to these two United States patents both directly and indirectly.

The frenum lock or natural expression former of this invention comprises a precontured plate 10 having a pair of spaced end or wing portions 11 and a medial connecting portion 12. The plate 10 is preferably of transparent vinyl plastic and is thin, being as little as 0.009 of an inch in thickness, or even thinner. Although termed a plate, it is not flat, but is generally curved transversely to fit the dental arch, and is also curved at right angles to the transverse curvature substantially throughout, thereby having an inherent double curvature which renders it form-sustaining. The material of the plate 10 is normally substantially inelastic and is characteristically resilient so that it retains its inherent double curvature and tends always to return to its precontoured shape, yet the material of the plate is flexible to permit fitting the former to almost any mouth without necessity for alterations. A series of sharp spurs 20 are raised from the plate 10 in strategic positions to engage and hold the musculature around the mouth.

In this case the wing portions 11 are of generally no greater curvature than the medial connection 12 and in fact curve less transversely, particularly toward the more-or-less tapered ends 11a. The bite indentation comprises a transverse ridge 24 formed in congruity with the double curvature of the plate 10 by the forward offset of the upper portion 16 of the plate from the lower portion 17. Since the upper portion may at times be used as the lower portion, as will shortly be explained, it will be convenient to refer to the portion 16 as the upper portion, whichever way the former is employed. Both upper and lower portions still possess double curvature, the curvature of one portion merely continuing that of the other after the offset, as appears in the sectional view of FIG. 3. The ridge formed by such offset is smooth vertically, blending into the upper and lower portions naturally. It extends transversely at least across the medial connecting section and preferably, as in the illustrated case, extends well around the sides of the former into the wing portions 11, gradually decreasing in size, always blending into the double curvature, and finally fading into the reduced inherent curvature near the ends of the wing portions.

This precontoured transverse ridge 24 serves many purposes and constitutes a marked improvement in expression formers. First it serves as a bite indentation for accommodation of overbite or underbite, as illustrated in FIGS. 4 and 5 respectively. Actually, very few persons have incisors which occlude perfectly when the lower jaw is in a relaxed position, and usually there is some degree of overbite as in FIG. 4. Nonocclusion in the reverse direction (underbite) is more rare, yet not infrequent. The transverse ridge or bite indentation preformed into the instant natural expression former is designed to fit either type of mouth more closely and naturally. Since overbite is much more common, the former will normally be used in the manner shown in FIG. 4, where the lower jaw is slightly offset to the rear of the upper. While the expression former of this invention is thus normally constructed with only a moderate amount of offset, forming a ridge which is not large in proportion to the overall size of the former, it will be recognized that formers may be manufactured with larger amounts of bite indentation to accommodate extreme cases of overbite or underbite more accurately. However, the flexibility of the illustrated expression former permits adapting the same to most mouths.

A related purpose of the preformed bite indentation is to provide a guide for normal relative positioning of the incisors, and thus, the jaws giving a more relaxed appearance to the face. Because of its improved form and inherent strength, the expression former is capable of serving, in conjunction with the injection needles and accompanying wire, as a stabilizer for the lower jaw. While the wire serves to support the lower jaw, the expression former itself is needed to aid in the normally slightly rearward positioning thereof with respect to the upper jaw. When fitted into position as shown in FIG.

4 the bite indentation holds the incisors and therefore the jaws in optimum relative position for a normal facial expression. In the case of underbite the former serves the same purpose when inverted, as illustrated in FIG. 5.

When installed with injector needles 30 and the accompanying twisted wire 32, as illustrated in FIG. 2, the end wire 32 is twisted and its looped end is inserted into one of the laterally spaced apertures 14 provided for this purpose in the rearwardly offset portion 17. Apertures 15 are also provided in the upper portion 16 to increase ventilation, and these may be used in the same manner as apertures 14 if convenient in the case of extra full lip tissue when any bulging caused thereby will not be apparent to the observer.

While the bite indentation serves as a positioner and stabilizer for the lower jaw, the incisors positioned therein tend to stabilize the expression former itself by engagement with the ridge 24. This accomplishes another purpose of the bite indentation, which is to render the expression former more stable in the mouth during the trial and error positioning of the musculature to form a natural expression. It operates in this manner, of course, whether the former is being used in a mouth having a characteristic overbite as in FIG. 4 or a characteristic underbite as in FIG. 5.

A further advantage of the bite indentation is the fact that it imparts greater strength to the expression former, thereby permitting the use of thinner material than heretofore possible. It will be observed that the ridge 24 extends substantially forwardly and generally in the plane of transverse curvature of the expression former. The ridge is the largest in the medial section 12 of the former and decreases in size toward the ends, as previously described, blending into the vertical curvature of the plate and thereby imparting a degree of double curvature of its own to the plate, supplementing the coexisting double curvature of the plate itself. Also, it can be seen, particularly in FIG. 3, that the curvature vertically of the upper portion is offset not only forwardly of the lower portion because of the ridge, but also at a slight angle thereto. The collective effect of the rounded edge or the ridge and the displaced and angularly offset curvatures of the upper and lower portions is to impart a greater degree of strength to the former than would be the case if the ridge were not present. The same effect could be achieved without a ridge by an increased double curvature in the medial connection, but a natural appearance of the mouth could not then be obtained. The result is a stronger, yet flexible and more adaptable expression former which provides a closer fit with the teeth and thus becomes even less likely to be noticed by an observer. The increased strength of the plate also provides a more firm base for support of the musculature around the mouth as it is engaged with the spurs 20.

A still further advantage produced by the bite indentation is that, since the material used may now be thinner, the spurs 20 raised from the plate 10 are also thinner and therefore sharper. The spurs may therefore be made smaller than heretofore possible to avoid excessive mutilation of the tissues during adjustment of the facial expression.

Another very important advantage of the preformed bite indentation is its usability in an edentulous mouth, i.e. as a "denture replacer." In the absence of teeth or dentures the preformed offset of upper and lower portions simulate the natural offset more closely than would a smoothly curved expression former not having such an offset. To enhance its use as a denture replacer, another feature is included in the former, namely the closure guide lines 25 and 26. In the illustrated case these are horizontal raised lines impressed in the upper and lower portions, respectively, of the plate 10 during manufacture. Since the plate is preferably transparent, such markings which may be formed in or marked on the plate by means other than impression, provide approximate guides for closure of the jaws during installation. For this purpose the guide lines are normally spaced about three-fourths of an inch apart and about equally above and below the bite indentation ridge 24 as guides for positioning the gums with respect to the ridge. Such guide lines assist the operator when teeth or dentures are present, as well as in their absence.

In the drawings it is seen that in the medial connecting portion or the medial connecting section 12 that in the upper left part, see FIGS. 1, 2 and 6, there is a first dividing line 36 which forms a first flap 38. Then, in the upper medial portion 12 and on the right there is a second dividing line 40 and a second flap 42.

In the lower part of the medial dividing portion and on the left there is a third dividing line 44 which forms a third flap 46. Then, on the lower medial dividing portion and on the right there is a fourth dividing line 48 which forms a fourth flap 50.

At the junction of the dividing lines 36 and 40 there may be considered to be a point edge 52. Likewise, at the junctions of the dividing line 44 and dividing line 40 there may be considered to be a point edge 54.

It is seen that each of the flaps 38, 42, 46 and 50 are distict and separate from the expression form and that the inner part of each of the flaps connects with an adjacent wing-like portion.

The expression former can be prepared from a blank plastic and then formed into the desired configuration. The dividing lines can be manually cut or can be formed in the forming of the expression former.

I consider that the dividing lines and the flaps make it easier to work the expression former into the mouth of the corpse or cadaver. The expression former can be placed between the lips and the gums of the corpse or cadaver. This expression former permits a wider spreading of the expression wing-like portions on insertion of the former into the mouth of the corpse or cadaver and also permits greater adaptation of the former to the dental arch of the corpse.

The expression former or frenum lock is of a size and marginal shape to fit between the lips and cheeks and the gums and teeth of the corpse and to extend beyond the lips. Indeed, it extends materially beyond the orbicularis oris which encircles and to a degree controls the expression of the lips. The expression of the lips is not wholly controlled by the orbicularis oris muscle but is also controlled to an appreciable extent by muscles which radiate from the orbicularis oris. In order to restore a natural expression to the mouth it is necessary that the natural tension of each of these muscles be substantially restored, and especially those adjacent the corners of the mouth.

To accomplish this the expression former is provided with a series of spurs 20 surrounding the lips and in general directed towards the lip margins. These spurs are preferably arranged in two series, each series being generally oval in shape, and in each expression former including the wing-like portion 11. For example, the spurs are arranged in an oval close to the lip margins and also are arranged in an outer oval. The spurs close to the lip margin are intended to pierce and to engage the orbicularis oris muscle and thereby retain the lips closed and the expression of the cadaver a normal expression. The outer oval of the spurs 22 engage primarily the radial musculature and prevent these muscles from sagging, thereby restoring the normal tension and the expression to them and to the face of the cadaver as a whole.

It is not sufficient to maintain the lips closed but the jaws must also be held closed. To accomplish holding the jaws closed there are used injector needles 30 and accompanying twisted wire 32 as illustrated and previously discussed.

In use, the expression former or frenum lock is inserted between the gums and the teeth and the lips and after the jaws have been closed properly and held, the plate is engaged by the spurs 20 with the muscles surrounding the lips, care being taken to restore the initial tension to the muscles so as to produce a natural expression in the corpse. Disengagement and reengagement with the muscles to achieve the desired result by trial and error is easily accomplished. If the plate is of a curvature greater than the dental arch of the corpse it may be flexed in the medial portion 12, especially, in view of the dividing lines and the flaps, without distortion or change in the shape of the wing-like portions 11 or cups 11 and without buckling at the relatively flat medial connection 12. Similarly, if the dental arch is of insufficiently great curvature the frenum lock may be bent outwardly to fit, without buckling, in the medial portion or medial connecting section, and without substantial distortion at any place of the fennum lock and also the lips of the cadaver.

The frenum lock or expression former may be formed of a suitable plastic such as polyethylene, methyl methacrylate, poly propylene and the like. The plastic should be a thermal plastic so that it can be readily formed under heat to the desired curvature. Again, the expression former may be formed from a blank piece of material and then under heat and pressure formed to the desired curvature. The spurs 20 may be formed by a suitable die as well as the apertures or passageways 14 and 15. Likewise, the dividing lines 36, 40, 44 and 48 may be formed by suitable dies or may be formed manually.

The former has a threefold purpose: to close the lips, to form the mouth, and to replace the dentures. In addition it cooperates with jaw-closing devices commonly used in preparing a cadaver for burial. The spurs are strategically located to support the general buccal musculature, and to facilitate forming the overall desired facial expression. Each spur is located to control a particular muscle. The inner spurs regulate the orbicularis oris as a whole and and support the lips in a proper position. The wing-like portions or cups 11 are precurved and maintain their curvature to the contour of the gums and teeth in the vertical direction as well as transversely.

In preparing this patent application I did not make a patent search. However, to repeat, I have two existing patents directed to a natural expression former, U.S. Pat. Nos. 3,103,052 and 3,195,215. I consider that this invention defines over each of the inventions in the aforementioned patents as in this invention there is recited the dividing lines and the flaps which make it possible for a person preparing a cadaver for burial to more easily insert the expression former into the mouth of the cadaver in between the mouth and the gums so as to permit wider spreading of the expression forming wing-like portions on insertion of the expression former into the mouth of the corpse and also permits a greater adaptation of the expression former to the dental arch of the cadaver.

From the foregoing and having presented my invention what I claim is:

1. An improvement in an expression former for insertion between the lips and the teeth and gums of a corpse, comprising a thin plate of resilient, limitedly flexible, yet substantially inelastic material, having an inherent form-sustaining double curvature overall to fit the curvature of the dental arch, said plate further having a marginal shape defining a pair of wing-like portions and a medial connecting section, and a size and shape to extend along the gums beyond the lips at all points, spurs on said plate for engagement with the mount musculature, an upper portion offset forwardly of a lower portion thereof at least in the medial section, and a substantially continuous wall connecting said offset portions thereof at least in the medial section, to define a transverse bite-indentation ridge therebetween extending along the line of nonocclusion of the forward teeth; and, wherein said improvement comprises:
   a. in said medial connecting section a first dividing line and a second dividing line;
   b. said first dividing line being in the direction of an adjacent wing portion and defining a first flap whose free end is distinct and separate from the medial connecting section;
   c. said second dividing line being in the direction of an adjacent wing portion and defining a second flap whose free end is distinct and separate from the medial connecting section;
   d. the inner part of the first flap connecting with an adjacent wing-like portion;
   e. the inner part of the second flap connecting with an adjacent wing-like portion;
   f. said first dividing line and said first flap and said second dividing line and said second flap permitting wider spreading of the expression forming wing-like portions on insertion into the mouth of the corpse and permitting greater adaptation to the dental arch of the corpse.

2. An improvement in an expression former for insertion between the lips and the teeth and gums of a corpse according to claim 1 comprising:
   a. said first dividing line and said second dividing line being in the upper portion of said medial connecting portion.

3. An improvement in an expression former for insertion between the lips and the teeth and gums of a corpse according to claim 1 comprising:
   a. said first dividing line and said second dividing line being in the lower portion of said medial connecting portion.

4. An improvement in an expression former for insertion between the lips and the teeth and gums of a corpse according to claim 1 comprising:
   a. said first dividing line and said second dividing line being in the upper portion of said medial connecting portion;
   b. a third dividing line in the lower portion of said medial connecting portion and being in the direction of an adjacent wing portion and defining a third flap whose free end is distinct and separate from the medial connecting section;

c. a fourth dividing line in the lower portion of said medial connecting section and being in the direction of an adjacent wing portion and defining a fourth flap whose free end is distinct and separate from the medial connecting section; and, d. said third dividing line and said third flap and said fourth dividing line and said fourth flap permitting wider spreading of the expression forming wing-like portions on insertion into the mouth of the corpse and permitting greater adaptation to the dental arch of the corpse.

5. An improvement in an expression former for insertion between the lips and the teeth and gums of a corpse according to claim 1 comprising:

a. the expression former defined in claim 1 wherein the plate is of transparent plastic material and further includes jaw closure guide markings on the medial section of said plate spaced above and below said ridge at distances indicating optimum jaw closure.

6. An improvement in an expression former for insertion between the lips and the teeth and gums of a corpse according to claim 4 comprising:

a. the expression former defined in claim 1 wherein the plate is of transparent plastic material and further includes jaw closure guide markings on the medial section of said plate spaced above and below said ridge at distances indicating optimum jaw closure.

7. An improvement in an expression former for insertion in the mouth of a corpse, comprising a thin, flexible plate having spurs thereon for engagement with the mouth musculature, and further having transversely spaced end portions to extend beyond the corners of the mouth and a frontal section connecting said end portions, said plate being of substantially form-retentive material and having an inherent curvature at least transversely of the mouth to fit the curvature of the dental arch, said plate further having upper and lower portions of shape and size to extend beyond the teeth between the gums and the lips, the upper portion being offset forwardly of the lower portion, and a connecting ridge between said upper and lower portions and extending transversely of the plate at least across said frontal section, said offset and ridge forming a bite indentation to accommodate nonocclusion of at least the forward teeth; wherein said improvement comprises:

a. in said frontal section a first dividing line and a second dividing line;

b. said first dividing line being in the direction of an adjacent end portion and defining a first flap whose free end is distinct and separate from the frontal section;

c. said second dividing line being in the direction of an adjacent end portion and defining a second flap whose free end is distinct and separate from the frontal section;

d. the inner part of the first flap connecting with an adjacent end portion;

e. the inner part of the second flap connecting with an adjacent end portion; and, f. said first dividing line and said first flap and said second dividing line and said second flap permitting wider spreading of the expression forming end portions on insertion into the mouth of the corpse and permitting greater adaptation to the dental arch of the corpse.

8. An improvement in an expression former for insertion in the mouth of a corpse according to claim 7 comprising:

a. the expression former defined in claim 3 wherein said plate is substantially symmetrical in over-all shape, otherwise than said offset and ridge, rendering the same invertible to accomodate nonocclusion of the teeth both in cases of underbite and overbite.

9. An improvement in an expression former for insertion in the mouth of a corpse according to claim 7 comprising:

a. the expression former defined in claim 3, said plate further having an inherent curvature also in the direction at right angles to such transverse curvature, imparting to said plate substantially form-sustaining double curvature in the upper and lower portions and in the end portions, said offset and connecting ridge extending along said transverse curvature beyond said frontal section and terminating in said end portions, thereby further rendering said plate from sustaining.

10. An improvement in an expression former for insertion in the mouth of a corpse according to claim 9 comprising:

a. the expression former defined in claim 5 wherein said plate is of substantially transparent, plastic material, said plate further having closure guide lines located on said upper and lower portions at least in the frontal section and spaced above and below said ridge at preselected distances, respectively, to indicate optimum jaw closure upon installation, particularly in an edentulous mouth.

11. An improvement in an expression former for insertion in the mouth of a corpse; said former having a marginal shape and size to fit between the lips and the teeth and gums and having an inherent form-sustaining double curvature generally overall, yet being flexible for fitting dental arches of differing curvatures, and further having spurs for engaging and holding the mouth tissues; a bite indentation simulator in said former, comprising upper and lower portions of said former, one of said portions protruding forwardly of the other at least in the region of the forward teeth of said corpse to form an offset along a line extending transversely of the mouth simulating nonocclusion of the teeth, a ridge integrally connecting said upper and lower portions along said offset line; said former having a central portion and an end portion on each side of said central portion: wherein said improvement comprises:

a. in said central portion a first dividing line and a second dividing line;

b. said first dividing line being in the direction of an adjacent end portion and defining a first flap whose free end is distinct and separate from the central portion;

c. said second dividing line being in the direction of an adjacent end portion and defining a second flap whose free end is distict and separate from the central portion;

d. the inner part of the first flap connecting with an adjacent end portion;

e. the inner part of the second flap connecting with an adjacent end portion; and, f. said first dividing line and said first flap and said second dividing line and said second flap permitting wider spreading of the expression forming end portions on insertion into the mouth of the corpse and permitting greater adaptation to the dental arch of the corpse.

12. A method for permitting wider spreading of the end portions of an expression former upon insertion of the expression former into the mouth of a corpse and permitting greater adaptation of the dental former to the arch of the corpse wherein said expression former comprises a thin, flexible plate of resilient, limitedly flexible, yet substantially inelastic material, having an inherent form-sustaining double curvature overall to fit the curvature of the dental arch, said plate further having a marginal shape defining a pair of wing-like portions and a medial connecting section, and a size and shape to extend along the gums beyond the lips at all points, spurs on said plate for engagement with the mouth musculature, an upper portion offset forwardly of a lower portion thereof at least in the medial section, and a substantially continuous wall connecting said offset portions thereof at least in the medial section, to define a transverse bite-indentation ridge therebetween extending along the line of nonocclusion of the forward teeth; and wherein said method comprises:

a. forming in said frontal section a first dividing line in the direction of an adjacent end portion and defining a first flap whose free end is distinct and separate from the frontal section and whose inner part connects with an adjacent end portion;

b. forming in said frontal section a second dividing line in the direction of an adjacent portion and defining a second flap whose free end is distinct and separate from the frontal section and whose inner part connects with an adjacent end portion; and, c. forming said first dividing line and said second dividing line in opposed direction.

* * * * *